United States Patent [19]

Rappaport

[11] Patent Number: 4,889,808
[45] Date of Patent: Dec. 26, 1989

[54] METHOD OF ENCHANCING T-PA AND SCU-PA PRODUCTION

[75] Inventor: Ruth Rappaport, Radnor, Pa.

[73] Assignee: American Home Products, New York, N.Y.

[21] Appl. No.: 907,004

[22] Filed: Sep. 17, 1986

Related U.S. Application Data

[63] Continuation-in-part of Ser. No. 782,658, Oct. 1, 1985, abandoned.

[51] Int. Cl.$^4$ .......................... C12N 5/02; C12N 9/72; A61K 37/64
[52] U.S. Cl. ............... 435/240.1; 435/240.2; 435/240.21; 435/240.25; 435/244; 435/215; 435/212; 435/226; 435/69.4; 435/183; 435/216; 435/948; 424/94.1; 424/94.63; 424/94.64; 514/8; 514/21; 514/56
[58] Field of Search ............... 435/68, 240, 244, 215, 435/212, 226, 948, 216, 240.2, 240.21, 240.25, 216

[56] References Cited

U.S. PATENT DOCUMENTS

| | | | |
|---|---|---|---|
| 4,505,893 | 3/1985 | Mori et al. | 424/94.64 |
| 4,520,107 | 5/1985 | Healy et al. | 435/244 |
| 4,661,453 | 4/1987 | Pollard | 435/215 |
| 4,752,603 | 6/1988 | Collen et al. | 424/94.64 |
| 4,757,005 | 7/1988 | Chen | 435/240.2 |
| 4,798,796 | 1/1989 | Wilson | 435/240.21 |

FOREIGN PATENT DOCUMENTS 0251806 1/1988 European Pat. Off. .
1271987 12/1986 Japan .................................. 435/215

OTHER PUBLICATIONS

Schreiber et al., *PNAS*, vol. 82, 1985, pp. 6138–6142.
Kadouri et al., *Advances in Biotechnological Processes*, vol. 5, 1985, pp. 275–99.
Rappaport et al., *Throm. Haemostasis*, 59(3), pp. 514–22, 1988, vol. 86 of Biological Abstracts #72977.
Chen et al., *J. Immunol.*, 132(6), 1984, p. 2955.
Vairel et al., *Thrombosis Res.* 30, 1983, pp. 219–224.
Paques et al., CA vol. 105, 1986, #543356.
Hamilton et al., *Biochem Biophys. Res. Comm.* 122(1), 1984, pp. 230–36.
Davies et al., *Science* 221, 1983, pp. 171–73.

*Primary Examiner*—Garnette D. Draper
*Attorney, Agent, or Firm*—Arthur G. Seifert

[57] ABSTRACT

Disclosed herein is a method of enhancing the production of tissue plasminogen activator (t-PA) and single chain urokinase plasminogen activator (SCU-PA) by normal human lung diploid fibroblast cells in a serum-free medium. The method comprises the addition of heparin (or low molecular weight heparin) and an endothelial cell growth factor to the culture medium.

39 Claims, No Drawings

METHOD OF ENCHANCING T-PA AND SCU-PA PRODUCTION

This Application is a continuation-in-part of Applicant's co-pending application Ser. No. 782,658, filed Oct. 1, 1985, now abandoned.

This invention provides a method of enhancing the production of t-PA (tissue plasminogen activator) and SCU-PA (single chain urokinase plasminogen activator) by normal human diploid lung fibroblast cells in a serum-free medium. The method comprises the addition of both heparin and an endothelial cell growth factor to the culture medium.

BACKGROUND OF THE INVENTION

Plasminogen activators (PAs) are serine proteases with trypsin-like specificity that convert the proenzyme plasminogen to the enzyme plasmin. Plasmin, in turn, is the primary agent of fibrinolysis in the blood stream where it degrades the fibrin network of a blood clot to form soluble products. The two known primary human plasminogen activators are tissue plasminogen activator (t-PA) and single chain urokinase plasminogen activator (SCU-PA), the latter being the proenzyme of urokinase (UK).

T-PA, a 63–65K protein, is secreted by numerous mammalian endothelial cells including aortic and venous endothelial cells. T-PA also has a high affinity for fibrin. For these reasons, t-PA is thought to be generated and to act directly at the site of a thrombus. SCU-PA, a 55K single chain protein, on the other hand, is thought to arrive at the site of a thrombus via the blood stream.

T-PA and SCU-PA, UK and streptokinase (SK, a third plasminogen activator), as well as modifications thereof, are under intense study to determine their respective physiological roles in thrombolysis, angiogenesis, metastasis, inflammation and ovulation. Such studies include clinical studies of the use of these substances in treating thrombosis. Such investigations also include the search for means for producing larger quantitites of these enzymes from normal human cells for use as thrombolytic agents. Additionally, such increased levels of production of the enzymes themselves would also give rise to elevated levels of the respective messenger RNA's (mRNA's). The availability of increased yields of the mRNA's would, in turn, enhance production of the enzymes, or modifications thereof, by recombinant DNA production methods.

For a recent review of plasminogen activators, particularly t-PA, UK and SCU-PA, see Cederholm-Williams, S.A., "Molecular Biology of Plasminogen activators and recombinant DNA progress", *Bio Essays*, 1, 168–173 (1984).

Currently, the main (non-recombinant) source of t-PA in larger quantities is Bowes melanoma cells. These malignant cells yield sufficient t-PA for the purification and characterization of the enzyme and for preparation of monoclonal and polyclonal antibodies. Additionally, they produce sufficient specific messenger RNA (mRNA) to allow complete gene cloning. However, a source of t-PA and its messenger RNA from normal (i.e. non-malignant) cells is sought. Such a source is needed which will produce a large amount of t-PA from a serum-free medium and permit isolation of significant amounts of mRNA from the cells. The presence of serum greatly affects t-PA production and recovery due to the presence of t-PA inhibitor and a variety of proteins found in serum.

Two recent journal articles report on the production of PA from normal human cells. First, A. Kadouri and Z. Bohak, "Production of Plasminogen Activator In Cultures of Normal Fibroblasts", *Biotechnology*, June 1983, pp. 354–358, report on the production of plasminogen activator (PA) from several different strains of lung fibroblasts. They particularly studied the production of PA from the IMR-90 human diploid fibroblasts with different sera and with culture plates coated with poly-D-lysine. Two experiments were also reported in which a serum medium was used first, and thereafter, the medium was changed to a serum-free medium supplemented with 0.5 percent lactalbumin hydrolyzate for a few days production (see FIGS. 1(b) and 2(b) on page 356 thereof). A batch and a continuous production process were also studied, but the medium used for these experiments was not clearly identified. The article does not recognize that there are two distinct PA's produced by the cells.

In the second paper, Gerard C. Brouty-Boye et al., "Biosynthesis of Human Tissue-Type Plasminogen Activator By Normal Cells", *Biotechnology*, December, 1984, pp. 1058–1062, the authors report on the production of t-PA from human embryonic lung (HEL) cells in a serum-free medium. They studied the use of eight different possible inducers to stimulate the t-PA production from these cells. These potential inducers were calcitonin (salmon), cholera toxin, colchicin, concanavalin A, glycine, glycylglycine, heparin, lactalbumin, sodium butyrate, α-thrombin, and ultraviolet light. Of these, only concanavalin A significantly (4 times) enhanced production over that without an inducer. The authors also noted that no synergistic effects between concanavalin A and the other tested substances were seen.

Applicant's invention comprises the use of a combination of heparin and endothelial cell growth factor (ECGF) to enhance the production of t-PA and SCU-PA by normal human diploid lung fibroblast cells in a serum-free medium. ECGF is an extract from bovine hypothalmus or pituitary gland which stimulates the growth of bovine and human venous or aortic endothelial cells. (See Maciag, T. et al., *Proceedings of the National Academy of Science*, 76, pp. 5674–78 (1979) and Olander, J. et al., In Vitro, 16, p. 209 (1980)). ECGF is available commercially. Heparin at concentrations of 90 mcg/ml, has been reported to potentiate the stimulatory effect of ECGF on the proliferation of human umbilical vein endothelial (HUVE) cells and of endothelial cells from adult human blood vessels. No suggestion is made that these agents stimulate PA production by these cells. See Thornton, S. C. et al., *Science*, 222, p. 623 (1983). In this study the medium was supplemented with 20 percent fetal bovine serum. Maciag, T. et al., *Science*, 225, p. 932–5 (1984) have reported further that heparin has a strong binding affinity for ECGF as shown by the use of heparin-Sepharose chromatographic extraction of ECFG. Applicant's invention differs from the above in that the combination of ECGF and heparin has been found to significantly enhance the production of t-PA and SCU-PA by normal human lung fibroblast cultures in a serum-free medium. As described below, other endothelial cell polypeptide mitogens may be employed in this invention as endothelial cell growth factors, and, hence, hereinafter "ECGF" is used to denote endothelial cell growth factor itself, which can be isolated from bovine hypothalmus or pituitary gland. The words "an endothelial cell growth factor" as used hereinafter includes these other endothelial cell polypeptide mitogens.

DETAILED DESCRIPTION OF THE INVENTION

This invention provides a method of enhancing the production of tissue plasminogen activator (t-PA) and single chain urokinase plasminogen activator (SCU-PA) in normal human diploid lung lung fibroblast cell cultures in a serum-free medium comprising adding to said culture heparin or low molecular weight heparin and an endothelial cell growth factor. With respect to the standard (unpurified) commercially available ECGF, the ECGF is added to the serum free culture medium to a concentration of 5 mcg/ml to 220 mcg/ml, and the heparin or low molecular weight heparin is added to a concentration of 5 mcg/ml to 220 mcg/ml. With respect to such standard ECGF, a preferred concentration of heparin or low molecular weight heparin is 15 mcg/ml to 150 mcg/ml, and a preferred concentration of ECGF is 25 mcg/ml to 100 mcg/ml. A more preferred concentration of heparin or low molecular weight heparin is 30 mcg/ml to 100 mcg/ml, and a more preferred concentration of ECGF is 25 mcg/ml to 60 mcg/ml. Additionally, when the concentration of ECGF is below 15 mcg/ml, then a concentration of heparin of 30 mcg/ml or more is preferred. Similarly, when the concentration of heparin used is below 15 mcg/ml, then a concentration of ECFG of 25 mcg/ml or more is preferred. Heparin (standard molecular weight) is preferred to low molecular weight heparin. Although any strain of normal human diploid lung fibroblast cells may be used for the production of t-PA and SCU-PA according to the method of the invention, preferred strains are WI-38, MCR-5, IMR-90 and IMR-91. Most preferred is the WI-38 lung fibroblast cell strain.

This invention additionally provides a method of enhancing the production of tissue plasminogen activator (t-PA) in normal human diploid lung fibroblast cell cultures comprising adding to said culture heparin or low molecular weight heparin and an endothelial cell growth factor. With respect to the standard, (unpurified) commercially available ECGF, the ECGF is added to the serum free culture medium to a concentration of 5 mcg/ml to 220 mcg/ml, and the heparin or low molecular weight heparin is added to a concentration of 5 mcg/ml to 220 mcg/ml. The different preferred concentration ranges of heparin or low molecular weight heparin and of ECGF described (standard) above are the same for this aspect of the invention. Heparin is also preferred for this aspect of the invention. The preferred and most preferred lung fibroblast cell culture strains as described above for the production of both t-PA and SCU-PA are also preferred for the production of t-PA according to this aspect of the invention.

This invention further provides a method of enhancing the production of single chain urokinase plasminogen activator (SCU-PA) in normal human diploid lung fibroblast cell cultures comprising adding to said culture heparin or low molecular weight heparin and an endothelial cell growth factor. With respect to the standard (unpurified) commercially available ECGF, the ECGF is added to the serum free culture medium to a concentration of 5 mcg/ml to 220 mcg/ml, and the heparin or low molecular weight heparin is added to a concentration of 5 mcg/ml to 220 mcg/ml. The different preferred concentration ranges of heparin or low molecular weight heparin and of ECGF (standard) described above are the same for this aspect of the invention. Heparin is also preferred for this aspect of the invention. The preferred and most preferred lung fibroblast cell culture strains as described above for the production of both t-PA and SCU-PA are also preferred for the production of SCU-PA according to this aspect of the invention.

Endothelial cell growth factor (ECGF) and heparin are both available commercially. One source of the standard ECGF used in the practice of the invention was Collaborative Research, Inc., Lexington, Mass. Their ECGF (denoted "endothelial cell growth supplement" or "CR-ECGS") is prepared from bovine hypothalmus. A second source of the standard ECGF was Seragen, Inc., Boston, Mass., whose material is prepared from bovine pituitary gland. Tables I-V below demonstrate the production of t-PA and SCU-PA according to the invention using the standard ECGF. There are a number of reliable commercial sources of heparin. "Low molecular weight heparin" as referred to herein means a depolymerized heparin having a mean molecular weight of less than 15,000. The low molecular weight heparin utilized in the practice of the invention is described in U.S. Pat. No. 4,281,108 and has a mean molecular weight of about 5000.

In addition to the endothelial cell growth factors described above (ECGF and p-ECGF), which are isolated from bovine hypothalmus and bovine pituitary gland, other endothelial cell growth factors have been isolated and characterized. Thus, there is a family of endothelial cell polypeptide mitogens which are identified as endothelial cell growth factors and which are included in the term endothelial cell growth factor as used herein. Thus, Alan B. Schreiber et al., The Journal of Cell Biology, 101, 1623–1626 (1985) determined that acidic brain-derived fibroblast growth factor (acidic FGF), and bovine eye-derived growth factor-II (EDGF-II) belong to this endothelial cell growth factor (ECGF) family. They proposed further that $\alpha$-heparin-binding growth factor ($\alpha$-HGF), acidic hypothalmus-derived growth factor (acidic HDGF), and retina derived growth factor (RDGF) would also be determined to belong to this endothelial cell growth factor (ECGF) family. Indeed, a hypothalmus derived growth factor is useful in the practice of this invention.

Schreiber et al. above, page 1625, describe the following factors which were used to establish that a particular endothelial cell polypeptide mitogen belonged to the subject endothelial cell growth factor family: (a) heparin affinity, (b) cross-reactivity to polyclonal ECGF antisera and monoclonal ECGF antibodies, (c) competition with ECGF for binding to a high affinity endothelial cell-derived receptor, and (d) potent biological activity as endothelial cell mitogens which is potentiated by heparin. Additionally, antibodies prepared against ECGF inhibited the mitogenic activity of acidic FGF and EDGF-II, giving further evidence of the family relationship. Thus, endothelial cell growth factors exhibiting such characteristics, particularly (a), (c) and (d), are included as endothelial cell growth factors for the practice of this invention. Preparation and purification of various known endothelial cell growth factors is described in the literature. For example, the extraction and purification of acidic FGF is described in Thomas, K. et al., Proceeding of the National Academy of Sciences, U.S.A., 81, 357–361 (1984).

Tables VI, VII and VIII demonstrate the production of t-PA and SCU-PA according to the invention using purified endothelial cell growth factor "p-ECGF". Purified ECGF is also available commerically from Collaborative Research, Inc. of Lexington, Mass. This material is prepared according to the method of Burgess, W. H. et al., Journal of Biological Chemistry, 260, 11,389–11,392 (1985) and has a purity of 90 percent or greater. When used in the production of t-PA and/or SCU-PA according to the invention, purified ECGF (p-ECGF) is added to the culture medium in concentrations of 25 nanograms/ml (ng/ml) or greater. A preferred concentration range of purified ECGF is 50 nanograms/ml to 500 nanograms/ml. A particularly preferred concentration of purified ECGF is 100 nanograms/ml to 300 nanograms/ml.

Table I below shows the potentiating effect of the combination of the invention, heparin and ECGF, on the production of t-PA from the WI-38 and MRC-5 strains of human diploid lung fibroblast cells. In these procedures heparin was employed at a concentration of 90 mcg/ml and ECGF at a concentration of 50 mcg/ml.

TABLE I

Dependence of t-PA production by normal human fibroblasts on the presence of both ECGF and heparin in serum-free medium

| Cell Type | Lot No.[a] tc | Time (hr) | none | RPMI-1640 heparin[b] | plus ECGF[c] | heparin/ ECGF |
|---|---|---|---|---|---|---|
| | | | | t-PA[d] (ng/well) | | |
| WI-38 | C8/tc 28 | 24 | 0 | 0 | 0.3 | 22.6 |
| | | 46 | 0 | 0 | 16.5 | 136.6 |
| | | 96 | 0 | 0 | 7.1 | 193.1 |
| WI-38 | C9/tc 24 | 24 | 0 | 0 | 13.9 | 33.9 |
| | | 46 | 4.2 | 15.9 | 31.0 | 146.0 |
| | | 96 | 8.8 | 19.7 | 31.0 | 192.2 |
| WI-38 | C14/tc 25 | 24 | 8.1 | 14.9 | 32.3 | 72.0 |
| | | 46 | 13.0 | 26.8 | 34.9 | 154.7 |
| | | 96 | 15.5 | 15.2 | 25.9 | 220.6 |
| MRC-5 | tc 25 | 24 | 9.7 | 10.5 | 28.2 | 43.3 |
| | | 96 | 22.4 | 26.9 | 35.3 | 256.7 |

[a]Lot No. refers to individual cultures lyophilized at different times. t.c. indicates the tissue culture passage level (i.e., the number of times the culture has been passaged, usually by doubling)
[b]heparin was employed at a concentration of 90 mcg/ml.
[c]ECGF (endothelial cell growth factor) as employed at a concentration of 50 mcg/ml.
[d]t-PA (tissue plasminogen activator) was determined by ELISA assay, employing IgG directed against purified human uterine t-PA.

For these studies, the cultures were grown to confluency in 24 well tissue culture plates employing RPMI-1640 supplemented with 10% fetal bovine serum and gentamycin. At confluency, the serum-containing medium was removed from the wells and the cells were washed two or three times with phosphate-buffered saline. RPMI-1640 medium with or without additives (i.e., heparin, ECGF, or heparin/ECGF) was added to the wells (1 ml per well) and aliquots removed at the indicated times for assay. Aliquots from quadruplicate wells were pooled and Tween-80 was added to a final concentration of 0.01 percent. The samples were stored at 4° C. until assayed. T-PA was assayed using a standard ELISA assay kit obtained from American Diagnostica, Greenwich, Conn. The ELISA assay for SCU-PA was developed as described below.

In Tables IIA and IIB below the production of t-PA is measured with unsupplemented medium and with medium supplemented with ECGF alone, with heparin alone, and with ECGF/heparin—all at varying concentrations of ECGF and heparin. The studies shown in Tables IIA and IIB were conducted in the same manner as described above with respect to Table I. WI-38 (TC 25) human diploid fibroblast cells were used.

TABLE IIA

Production of t-PA with ECGF, Heparin and ECGF/Heparin in varying concentrations

| | Medium | Time (Hours) t-PA (ng/well) | | | | | | |
|---|---|---|---|---|---|---|---|---|
| | | 7 | 16 | 25 | 30 | 42 | 50 | 62 |
| 1A | RPMI | 5 | 9 | 11 | 15 | 19 | 17 | 19 |
| 2. | 5 μg ECGF | 7 | 23 | 29 | 32 | 36 | 32 | 32 |
| 3. | 10 μg ECFG | 7 | 36 | 51 | 67 | 77 | 75 | 79 |
| 4. | 25 μg ECGF | 10 | 42 | 50 | 73 | 77 | 80 | 78 |
| 5. | 50 μg ECGF | 12 | 38 | 58 | 85 | 94 | 92 | 103 |
| 6. | 100 μg ECGF | 11 | 43 | 64 | 93 | 113 | 115 | 121 |
| 7. | 200 μg ECGF | 13 | 54 | 83 | 116 | 145 | 152 | 163 |
| 8. | 5 μg ECGF + 90 μg Hep. | 13 | 51 | 85 | 140 | 194 | 217 | 243 |
| 9. | 10 μg ECGF + 90 μg Hep. | 12 | 55 | 86 | 131 | 171 | 184 | 239 |
| 10. | 25 μg ECGF + 90 μg Hep. | 14 | 68 | 105 | 151 | 207 | 222 | 300 |
| 11. | 50 μg ECGF + 90 μg Hep. | 12 | 83 | 107 | 150 | 194 | 229 | 307 |
| 12. | 100 μg ECGF + 90 μg Hep. | 15 | 65 | 107 | 148 | 196 | 241 | 350 |
| 13. | 200 μg ECGF + 90 μg Hep. | 20 | 76 | 128 | 175 | 258 | 305 | 421 |

TABLE IIB

Production of t-PA with ECGF, Heparin and ECGF/Heparin at varying concentrations

| | Medium | Time (Hours) (t-PA ng/well) | | | | | | |
|---|---|---|---|---|---|---|---|---|
| | | 7 | 16 | 25 | 30 | 42 | 50 | 62 |
| 1B | RPMI | 5 | 8 | 7 | 10 | 9 | 15 | 18 |
| 14. | 5 μg Hep. | 5 | 7 | 12 | 12 | 19 | 23 | 28 |
| 15. | 15 μg Hep. | 4 | 8 | 7 | 7 | 9 | 20 | 19 |
| 16. | 30 μg Hep. | 6 | 7 | 11 | 9 | 12 | 14 | 15 |
| 17. | 90 μg Hep. | 6 | 8 | 10 | 10 | 11 | 20 | 20 |
| 18. | 180 μg Hep. | 7 | 8 | 20 | 14 | 16 | 17 | 18 |
| 19. | 5 μg Hep. + 50 μg ECGF | 8 | 36 | 59 | 90 | 118 | 165 | 231 |
| 20. | 15 μg Hep. + 50 μg ECGF | 9 | 47 | 86 | 101 | 141 | 174 | 241 |
| 21. | 30 μg Hep. + 50 μg ECGF | 8 | 54 | 71 | 84 | 141 | 171 | 241 |
| 22. | 90 μg Hep. + 50 μg ECGF | 10 | 51 | 98 | 120 | 171 | 203 | 283 |
| 23. | 180 μg Hep. + 50 μg ECGF | 12 | 76 | 95 | 116 | 170 | 221 | 312 |

Table III below shows the production of t-PA and SCU-PA by Bowes melanoma cells with and without the combination of ECGF (50 mcg/ml) and heparin (90 mcg/ml). Bowes melanoma cells were the original source of purified t-PA. (These studies were conducted in the same manner as those in Table I.)

TABLE III

Production of t-PA and SCU-PA by Bowes Melanoma Cells with and without ECGF/Heparin (factors)

| Medium | Time (Hours) | | | | | |
|---|---|---|---|---|---|---|
| | 6 | 12 | 24 | 48 | 72 | 96 |
| | t-PA (ng/ml) | | | | | |
| no factors + | 15 | 25 | 65 | 140 | 215 | 225 |
| ECGF/Hep. | 15 | 40 | 95 | 160 | 195 | 180 |
| | SCU-PA (ng/ml) | | | | | |
| no factors + | 0[a] | 0 | 0 | 0 | 0 | 0 |

TABLE III-continued

Production of t-PA and SCU-PA by Bowes Melanoma
Cells with and without ECGF/Heparin (factors)

| Medium | Time (Hours) | | | | | |
|---|---|---|---|---|---|---|
| | 6 | 12 | 24 | 48 | 72 | 96 |
| ECGF/Hep. | 0 | 0 | 0 | 0 | 0 | 0 |

$^a$0 indicates undetectable, that is, less than the sensitivity of the assay (approx. 1 ng).

These results show that the Bowes melanoma cells produced only t-PA, the level of which remained substantially the same with or without the addition of ECGF/heparin to the culture medium.

Table IV below shows the production of both t-PA and SCU-PA by WI-38 cells with and without the combination of ECGF and Heparin (50 mcg/ml and 90 mcg/ml respectively).

TABLE IV

Production of t-PA and SCU-PA by WI-38 Cells
with and without ECGF/Heparin (factors)

| Medium | Time (Days) | | | |
|---|---|---|---|---|
| | 3 | 4 | 5 | 6 |
| | t-PA (ng/ml) | | | |
| no factors + | 45 | 30 | 25 | 30 |
| ECGF/Hep. | 365 | 510 | 495 | 590 |
| | SCU-PA (ng/ml) | | | |
| no factors + | 0 | 0 | 5 | 5 |
| ECGF/Hep. | 240 | 335 | 300 | 320 |

These results establish that the addition of the combination of ECGF and Heparin to the human fibroblast cell culture medium substantially enhances production of both t-PA and SCU-PA.

Table V below shows the production of t-PA with and without the two factors (ECGF and heparin) with a recycling of the medium utilizing roller bottles. the tissue culture used was WI-38/TC27. In the first cycle the culture was grown in a 10 percent serum medium. This was removed by washing and replaced by the serum-free medium (RPMI) with and without the factors. (ECGF concentration was 50 mcg/ml and heparin concentration was 90 mcg/ml.) The data shown are for the days of each successive cycle in the serum-free medium. The ELISA t-PA assay described below was used.

TABLE V

Producton of t-PA with and without
factors (ECGF + Heparin) with recycling

| | | t-PA (ng/ml) | |
|---|---|---|---|
| | days | w/o factors | w. factors |
| cycle 1 | 2 | 15 | 150 |
| | 3 | 30 | 140 |
| | 4 | 25 | 130 |
| cycle 2 | 2 | 50 | 760 |
| | 3 | 100 | 1165 |
| | 4 | 240 | 1130 |
| cycle 3 | 2 | 600 | 650 |
| | 3 | 560 | 960 |
| | 4 | 500 | 910 |
| cycle 4 | 2 | 50 | 260 |

These results show that the combination of ECGF and heparin also greatly enhances the production of t-PA in a serum-free medium when the cells are recycled in a longer term production operation.

The level of production of t-PA by ECGF/heparin stimulated WI-38 cultures has thus been determined to be on the order of 200–1000 ng/$10^6$ cells/day. It has also been established that fibroblast diploid cells can be recycled at least two, and possibly three, times to product t-PA. Thus, as shown in Table V above, cultures which had been stimulated to product t-PA were refed after 48 hours with growth medium (containing 10% fetal bovine serum) and subsequently (after five days) restimulated in a serum-free, ECGF and heparin-containing medium. The results showed that the cells were capable of producing t-PA levels comparable to or greater than those observed after primary stimulation.

At maximal concentrations of the factors (ECGF at 50 mcg/ml and heparin at 90 mcg/ml) similar results have been obtained irrespective of whether the diploid fibroblasts were cultivated in tissue culture plates (which are grown in the presence of 95% air, 5% $CO_2$) or closed tissue culture flasks ranging in size from 25 $cm^2$ to 150 $cm^2$. The invention has been practiced successfully at the level of 200, 150 $cm^2$ flasks (total wet weight of cells about 8 grams) in the course of producing messenger RNA for recombinant work.

In Tables VI, VII and VIII below, the production of t-PA, SCU-PA and t-PA, respectively, is shown using heparin and purified ECGF, with varying concentrations of purified ECGF. WI-38 firoblast cells and a serum free medicine were used in these experiments. In all three experiments, heparin, where used, was at a concentration of 90 mcg/ml. In these tables the standard ECGF is indicated by "ECGF" and purified ECGF is indicated by "p-ECGF".

TABLE VI

Producton of t-PA with standard ECGF
and purified ECGF at varying concentrations

| | Medium | Time (Hours) | | | |
|---|---|---|---|---|---|
| | | 8 | 24 | 48 | 72 |
| | | t-PA (ng/well) | | | |
| 1. | RPMI alone | — | — | 10 | — |
| 2. | 50 μg/ml ECGF | 19 | 70 | 85 | 56 |
| 3. | 90 μg/ml hep. | 15 | 8 | 21 | 12 |
| 4. | 50 μg/ml ECGF + 90 μg/ml hep. | 20 | 71 | 218 | 320 |
| 5. | 50 ng/ml p-ECGF | — | 8 | 14 | — |
| 6. | 50 ng/ml p-ECGF + 90 μg/ml hep. | — | 17 | 59 | 46 |
| 7. | 100 ng/ml p-ECGF | — | 19 | 63 | — |
| 8. | 100 ng/ml p-ECGF + 90 μg/ml hep. | 2.8 | 37 | 99 | 200 |
| 9. | 200 ng/ml p-ECGF | 2.4 | 28 | 28 | — |
| 10. | 200 ng/ml p-ECGF + 90 μg/ml hep. | — | 64 | 188 | 437 |

TABLE VII

Production of SCU-PA with standard ECGF
and purified ECGF at varying concentrations

| | Medium | Time (Hours) | | | |
|---|---|---|---|---|---|
| | | 8 | 24 | 48 | 72 |
| | | SCU-PA (ng/well) | | | |
| 1. | RPMI alone | 32 | 22 | 47 | 134 |
| 2. | 50 μg/ml ECGF | 160 | 281 | 186 | 289 |
| 3. | 90 μg/ml hep. | 121 | 101 | 103 | 130 |
| 4. | 50 μg/ml ECGF + 90 μg/ml hep. | 127 | 279 | 256 | 575 |
| 5. | 50 ng/ml p-ECGF | 5.6 | 80 | 90 | 105 |
| 6. | 50 ng/ml p-ECGF + 90 μg/ml hep. | 5.1 | 305 | 229 | 323 |
| 7. | 100 ng/ml p-ECGF | — | 212 | 244 | 194 |
| 8. | 100 ng/ml p-ECGF + 90 μg/ml hep. | 36 | 258 | 249 | 541 |
| 9. | 200 μg/ml p-ECGF | 11 | 258 | 216 | 238 |
| 10. | 200 μg/ml p-ECGF + 90 μg/ml hep. | — | 289 | 308 | 730 |

TABLE VIII

Production of t-PA with standard ECGF and purified ECGF at varying concentrations

| | Medium | Time (Hours) | | | | |
|---|---|---|---|---|---|---|
| | | 8 | 12 | 24 | 48 | 72 |
| | | t-PA (ng/well) | | | | |
| 1. | RPMI alone | 4.1 | 3.4 | 4.7 | 5.0 | 9.5 |
| 2. | Hep.* | 5.4 | 6.6 | 9.4 | 14.3 | 14.6 |
| 3. | 50 µg/ml ECGF | 4.9 | 7.3 | 27.7 | 27.4 | 27.2 |
| 4. | 50 µg/ml ECGF + Hep. | 8.3 | 15.8 | 51.1 | 102.0 | 149.4 |
| 5. | 200 ng/ml p-ECGF | 5.1 | 8.1 | 26.7 | 17.3 | 13.7 |
| 6. | 200 ng/ml p-ECGF + Hep. | 6.6 | 11.4 | 37.1 | 76.4 | 79.6 |
| 7. | 100 ng/ml p-ECGF | 5.4 | 6.5 | 14.3 | 12.0 | 11 |
| 8. | 100 ng/ml p-ECGF + Hep. | 5.7 | 9.1 | 32.6 | 54 | 41.2 |
| 9. | 50 ng/ml p-ECGF | 4.6 | 5.6 | 8.9 | 7 | 10 |
| 10. | 50 ng/ml p-ECGF + Hep. | 5.5 | 5.9 | 20.4 | 25.6 | 22.6 |
| 11. | 25 ng/ml p-ECGF | 3.3 | 3.5 | 5.4 | 6.1 | 8.9 |
| 12. | 25 ng/ml p-ECGF + Hep. | 5.4 | 6.1 | 13.8 | 17.7 | 16.4 |
| 13. | 12.5 ng/ml p-ECGF | 3.4 | 5.1 | 4.4 | 5.4 | 7.7 |
| 14. | 12.5 ng/ml p-ECGF + Hep. | 4.9 | 3.3 | 9.2 | 14.1 | 12 |

*all heparin concentrations were 90 µg/ml.

Fibrin autography, $^{125}$I-fibrinolysis, immunoprecipitation, and ELISA assays were developed and utilized to measure t-PA and SCU-PA production both qualitatively and quantitatively. Anti-UK IgG was purified by ammonium sulfate precipitation and DEAE chromatography from goat antiserum directed against human urokinase (Abbokinase, Abbott Laboratories, Chicago, Ill.). The anti-UK IgG so prepared was found to be an excellent reagent for immunoprecipitation of SCU-PA from the supernatants of several human lung fibroblast cultures. This same antibody and a similarly prepared rabbit anti-UK lgG were employed to assay SCU-PA in a double sandwich ELISA assay. The data shown in Tables I–VIII above was determined by the appropriate ELISA assay.

In addition, a chromogenic assay for plasminogen activators (t-PA and SCU-PA) was adapted for use in microtiter plates. In this indirect assay, plasiminogen is converted to plasmin by t-PA or SCU-PA. Plasmin, in turn, cleaves the substrate, D-valyl-L-leucyl-L-lysine-p-nitroanilide, liberating the chromphore, p-nitroaniline, which is measured photometrically at 405 nm. The assay is linear over the range of 0.125 to 5.0 international units (IU) for SCU-PA and between 0.5 and 5 ng/ml for t-PA. With the availability of specific neutralizing antibodies against t-PA or SCU-PA, the assay can be used to estimate the relative amounts of each enzyme in complex mixtures.

Additional evidence documenting the production of SCU-PA and t-PA by normal human diploid lung fibroblasts was obtained primarily with the aid of two techniques: fibrin autography and immunoprecipitation. Both techniques rely on the resolution of the enzymes by SDS-acrylamide gel electrophoresis. In the case of fibrin autography, detection of electrophoretically distinct PAs is achieved by overlaying acrylamide gels with fibrin agar. In the presence of plasminogen, zones of clearing due to the degradation of fibrin by plasmin appear at positions occupied by molecules with PA activity.

In the case of immunoprecipitation, proteins metabolically labeled in situ with $^{35}$S-methionine are first reacted with specific antibodies. The immune complexes which develop are then selectively removed from the culture fluids by absorption on and subsequent elution from Protein A-Sepharose beads (Pharmacia).

$^{35}$S-methionine-labeled proteins, isolated in this manner, are resolved on SDS-acrylamide gels and their position is localized by exposure of the acrylamide gel to X-ray film.

By fibrin autography, two distinct electrophoretic species, each of which exhibited fibrinolytic activity, was detected in conditioned medium (serum-free) harvested from confluent cultures of diploid fibroblasts (WI-38). One of the electrophoretic species comigrated with single chain urokinase (SCU-PA) (55,000 $M_r$) and the other species comigrated with purified t-PA (63,000 to 65,000 $M_r$) and with the only fibrinolytic enzyme found in conditioned medium from Bowes melanoma cultures (also 63,000 to 65,000 $M_r$). When the acrylamide gels were overlayed with fibrin agar containing anti-urokinase IgG (150 µg/ml), the fibrinolytic enzyme from diploid cultures which comigrated with single chain urokinase and single chain urokinase were neutralized (i.e., zones of clearing due to SCU-PA in the absence of antibody disappeared in the presence of anti-urokinase IgG). Similarly, when acrylamide gels were overlayed with fibrin agar containing anti-t-PA IgG (50 µg/ml), zones of clearing attributable to the fibrinolytic enzyme from diploid cultures which comigrated with purified t-PA, purified t-PA, and the fibrinolytic enzyme from Bowes' conditioned medium all disappeared.

The data derived from immunoprecipitation studies confirmed and extended the results of the previous assays. With this technique, it was possible to establish the molecular weight of the enzymes precipitated with specific antibody by comparing their relative mobilites with $^{14}$C-labeled proteins of known molecular weight. Using specific anti-t-PA IgG prepared against Bowes melanoma t-PA and specific anti-UK IgG (purified from serum against Abbokinase), it was established that the two fibrinolytic enzymes found in WI-38 diploid fibroblast cultures corresponded to proteins of molecular weight 63,–65,000M and 55,000 $M_r$, the molecular weights, respectively, of Bowes melanoma t-PA and human single chain urokinase (SCU-PA). This identification could not be made by fibrin autography because treatment of the enzymes with reducing agent, a mandatory step in the determination of molecular weight, destroyed fibrinolytic activity. The immunoprecipitation data confirmed that Bowes melanoma cells produce only t-PA since no SCU-PA could be precipitated with anti-UK IgG under conditions whereby SCU-PA was precipitated from diploid culture fluids. The data also showed that ECGF and heparin elevated both t-PA and SCU-PA since the amount of immunopecipitatable t-PA and SCU-PA increased when cells were cultivated in the presence of these additives.

These assay results, together with the ELISA results shown in Tables I–VIII, show that human diploid lung fibroblasts derived from fetal lung tissue produce two fibrinolytic enzymes, a urokinase-type and a tissue-type plasminogen activator. The level of production of both enzymes is significantly enhanced by the addition of a combination of ECGF and heparin to the culture medium. The increased production of t-PA and SCU-PA thus obtained is sufficient to allow the isolation of specific t-PA and SCU-PA mRNA from such normal human diploid lung fibroblast cells.

This invention further provides a method of stimulating the production of t-PA and SCU-PA in mammals, a method of treating thrombosis in mammals, and a pharmaceutical composition. These aspects of the invention are described below.

Current evidence indicates that members of a family of endothelial cell polypeptide growth factors or mitogens play an important role in blood vessel homeostasis (Maciag T., Progress in Thrombosis and Hemostasis, 7, 167 (1984)). These factors are thought to act as specific and potent regulators of endothelial cell migration and proliferation in the process of neovascularization by which new blood vessels are formed (i.e. angiogenesis). The biological activity of these factors is believed to be mediated by a high-affinity polypeptide receptor present on the endothelial cell surface and is potentiated by a structural interaction with the glycosaminoglycan heparin (Schreiber, A. B., et al., Proc. Nat'l. Acad. Sci., U.S.A., 82: 6,138, 1985; Friesel, R et al., J. Biol. Chem. 261: 7,581, 1986). Interaction of endothelial cell growth factor with receptors on cells other than endothelial cells including human foreskin fibroblasts, murine BALB/c 3T3 fibroblasts, human epidermoid carcinoma (A-431) and human alveolar carcinoma (A-549) was also reported by these authors.

In the in vitro aspect of the present invention, described above, an endothelial cell growth factor and heparin stimulate human diploid lung fibroblast cells to produce t-PA and SCU-PA. A further aspect of the present invention provides a method of stimulating the production of tissue plasminogen activator (t-PA) and single chain urokinase plasminogen activator (SCU-PA) in a mammal, including man, in need thereof, comprising administering to said mammal an effective amount of heparin or low molecular weight heparin and an endothelial cell growth factor. The endothelial cell polypeptide mitogens described above, namely ECGF, acidic FGF, EDGF-II, α-HGF, acidic HDGF and FDGF, are useful for this in vivo aspect of the invention also. ECGF, acidic FGF and EDGF-II are preferred for this aspect of the invention, and ECGF is most preferred. Means of administration in which the combination of heparin or low molecular weight heparin and an endothelial cell growth factor is delivered directly to the site of a thrombus or potential thrombus are preferred. Thus, intravenous, intracoronary or similar routes of administration (e.g., by injection or infusion) are preferred.

As noted with respect to the background of the present invention, given above, t-PA and SCU-PA are endogenous thrombolytic agents, which act in blood vessels by converting plasminogen to plasmin. Heparin itself is used in treatment, often in conjunction with various types of surgery, including coronary surgery, as an antithrombotic agent. In the present aspect of the subject invention, heparin or low molecular weight heparin and an endothelial cell growth factor are used to stimulate endogenous (in vivo) production of t-PA and/or SCU-PA. Thus, the administration of heparin or low molecular weight heparin and an endothelial cell growth factor according to the invention is useful in the treatment of thrombosis. Additionally, the potentiating effect between heparin and an endothelial cell growth factor in producing t-PA and/or SCU-PA in vivo allows the administration of lower levels of heparin (or low molecular weight heparin) for use as an antithrombotic agent, than is presently required. A major side effect of heparin therapy is bleeding. Further, Spann, J. F. et al., Drugs, 28, 465–483, at 478 (1984), report that reocclusion after breakup of a coronary blood clot (by intracoronary administration of streptokinase) occurred in an average of 17 percent of a group of 159 patents studied, in spite of early intravenous heparin treatment. The administration of heparin or low molecular weight heparin and an endothelial cell growth factor according to the invention would also be useful in preventing such reocclusion by stimulating endogenous levels of t-PA or SCU-PA. In attempting to prevent such reocclusion, Spann et al., above, report the use of doses of heparin from 30,000 units per day (approx. 3 mg/kg/day) to the dose necessary to achieve partial thromboplastin time greater than 2 to 3 times normal. Due to the ability of heparin or low molecular weight heparin and an endothelial cell growth factor, when administered according to the present invention, to stimulate the endogenous production of t-PA and SCU-PA, the doses of heparin itself used in preventing such reocclusion according to the invention would be greatly reduced. The advantage of Applicant's invention is in the ability to stimulate endogenous t-PA and/or SCU-PA production under conditions in which the systemic threat of bleeding due to high doses of heparin is reduced. See Bergmann, S. R. et al., Science, 220, 1181–1183 (1983).

Particularly for use in stimulating the in vivo production of t-PA and/or SCU-PA in a mammal, including man, in need thereof, preferred doses of heparin or low molecular weight heparin are 0.1–5.0 mg/kg/day (approx. 1,100–50,000 units per day), and preferred doses of an endothelial cell growth factor are 0.1–5.0 mg/kg/day. A more preferred dose of heparin is 0.1 to 2.0 mg/kg/day. Such doses may vary depending upon the particular subject and the severity of the condition. For treating thrombosis, higher doses may be required to effect complete thrombolysis (clot dissolution). Man is the preferred mammal for administration. Determination of effective doses of heparin or low molecular weight heparin and an endothelial cell growth factor for a particular therapy is within the skill of the pharmacological and medical arts. Such determinations are based upon the monitoring of levels of t-PA, SCU-PA, fibrinolysis and other blood and circulatory factors. Particular thromboses which may be treated by the present invention include pulmonary, coronary, deep vein or cerebral. Of these, pulmonary or coronary are preferred, and pulmonary is most preferred.

In a still further aspect, this invention provides a pharmaceutical composition comprising a cell-free culture fluid (conditioned medium) containing an endothelial cell growth factor, heparin or low molecular weight heparin, t-PA and SCU-PA, said culture fluid being derived from a normal human diploid lung fibroblast culture in a serum-free to medium which heparin or low molecular weight heparin and said endothelial cell growth factor were added. T-PA and SCU-PA are present in said culture fluid due to their production by said culture. A refined form of this pharmaceutical composition, from which substances having a molecular weight above 75,000 and below 50,000 have been removed, thereby consisting substantially of t-PA and SCU-PA produced by said culture, is preferred. Such refinement would remove most of heparin or low molecular heparin and the endothelial cell growth factor and protease inhibitors, such as protease-nexin or plasminogen activator inhibitors. Such pharmaceutical composition in which the concentration of t-PA and SCU-PA produced by said culture is, independently, at least 100 ng/ml is further preferred.

The concentrations and preferred concentrations of ECGF, p-ECGF and heparin or low molecular weight heparin described above with respect to the method of producing t-PA and SCU-PA in vitro aspect of the invention also apply to the pharmaceutical composition aspect of the invention. Similarly, the endothelial cell growth factors ECGF, acidic FGF, EDGF-II, α-HGF, acidic HDGF and RDGF are preferred for this aspect of the invention also. EDGF, acidic FGF and EDGF-II are most preferred and ECGF is particularly preferred. Further preferred are the normal human diploid lung cells WI-38, MRC-5, IMR-90 and IMR-91, of which WI-38 is most preferred.

The unrefined and refined pharmaceutical compositions of the invention may be used particularly in thrombolytic therapy (to break up or dissolve blood clots) or antithrombotic therapy (to prevent blood clots from forming or reforming). When used in such therapy, preferred doses of the refined composition would contain 1–20 mg each of t-PA and SCU-PA. Lesser amounts of t-PA and SCU-PA in the unrefined composition may be required due to the ability of the heparin or low molecular weight heparin and the endothelial cell growth factor therein to stimulate the in vivo production of t-PA and SCU-PA.

What is claimed is:

1. A method of enhancing the production of tissue plasminogen activator (t-PA) and single chain urokinase plasminogen activator (SCU-PA) in normal human diploid lung fibroblast cell cultures in a serum-free medium comprising adding to said culture heparin or low molecular weight heparin and an endothelial cell growth factor.

2. A method according to claim 1 in which heparin is used.

3. A method according to claim 1 in which the concentration of heparin or low molecular weight heparin is from 5 mcg/ml to 220 mcg/ml.

4. A method according to claim 1 in which the concentration of heparin or low molecular weight heparin is 30 mcg/ml to 100 mcg/ml.

5. A method according to claim 1 in which the standard endothelial cell growth factor (ECGF) is used.

6. A method according to claim 5 in which the concentration of the standard ECGF is 5 mcg/ml to 220 mcg/ml.

7. A method according to claim 5 in which the concentration of the standard ECGF is 25 mcg/ml to 60 mcg/ml.

8. A method according to claim 1 in which purified endothelial cell growth factor (p-ECGF) is used.

9. A method according to claim 8 in which the concentration of p-ECGF is 50 ng/ml to 500 ng/ml.

10. A method according to claim 8 in which the concentration of p-ECGF is 100 ng/ml to 300 ng/ml.

11. A method according to claim 1 in which the endothelial cell growth factor is selected from endothelial cell growth factor (ECGF), acidic brain-derived fibroblast growth factor (acidic FGF), bovine eye-derived growth factor-II (EDGF-II), α-heparin-binding growth factor (α-HGF), acidic hypothalmus-derived growth factor (acidic HDGF), and retina derived growth factor (RDGF).

12. A method according to claim 1 in which the normal human diploid lung fibroblast cell culture is selected from WI-38, MRC-5, IMR-90 and IMR-91.

13. A method according to claim 1 in which the normal human diploid lung fibroblast cell culture is WI-38.

14. A method of enhancing the production of tissue plasminogen activator (t-PA) in normal human diploid lung fibroblast cell cultures in a serum-free medium comprising adding to said culture heparin or low molecular weight heparin and an endothelial cell growth factor.

15. A method according to claim 14 in which heparin is used.

16. A method according to claim 14 in which the concentration of heparin or low molecular weight heparin is from 5 mcg/ml to 220 mcg/ml.

17. A method according to claim 14 in which the concentration of heparin or low molecular weight heparin is 30 mcg/ml to 100 mcg/ml.

18. A method according to claim 14 in which the standard endothelial cell growth factor (ECGF) is used.

19. A method according to claim 18 in which the concentration of the standard ECGF is 5 mcg/ml to 220 mcg/ml.

20. A method according to claim 18 in which the concentration of the standard ECGF is 25 mcg/ml to 60 mcg/ml.

21. A method according to claim 14 in which purified endothelial cell growth factor (p-ECGF) is used.

22. A method according to claim 21 in which the concentration of p-ECGF is 50 ng/ml to 500 ng/ml.

23. A method according to claim 21 in which the concentration of p-ECGF is 100 ng/ml to 300 ng/ml.

24. A method according to claim 14 in which the endothelial cell growth factor is selected from endothelial cell growth factor (ECGF), acidic brain-derived fibroblast growth factor (acidic FGF), bovine eye-derived growt factor-II (EDGF-II), α-heparin-binding growth factor (α-HGF), acidic hypothalmus-derived growth factor (acidic HDGF), and retina derived growth factor (RDGF).

25. A method according to claim 14 in which the normal human diploid lung fibroblast cell culture is selected from WI-38, MRC-5, IMR-90 and IMR-91.

26. A method according to claim 14 in which the normal human diploid lung fibroblast cell culture is WI-38.

27. A method of enhancing the production of single chain urokinase plasminogen activator (SCU-PA) in normal human diploid lung fibroblast cell cultures in a serum-free medium comprising adding to said culture heparin or low molecular weight heparin and an endothelial cell growth factor.

28. A method according to claim 27 in which heparin is used.

29. A method according to claim 27 in which the concentration of heparin or low molecular weight heparin is from 5 mcg/ml to 220 mcg/ml.

30. A method according to claim 27 in which the concentration of heparin or low molecular weight heparin is 30 mcg/ml to 100 mcg/ml.

31. A method according to claim 27 in which the standard endothelial cell growth factor (ECGF) is used.

32. A method according to claim. 31 in which the concentration of the standard ECGF is 5 mcg/ml to 220 mcg/ml.

33. A method according to claim 31 in which the concentration of the standard ECGF is 25 mcg/ml to 60 mcg/ml.

34. A method according to claim 27 in which purified endothelial cell growth factor (p-ECGF) is used.

35. A method according to claim 34 in which the concentration of p-ECGF is 50 ng/ml to 500 ng/ml.

36. A method according to claim 34 in which the concentration of p-ECGF is 100 ng/ml to 300 ng/ml.

37. A method according to claim 27 in which the endothelial cell growth factor is selected from endothelial cell growth factor (ECGF), acidic brain-derived fibroblast growth factor (acidic FGF), bovine eye-derived growth factor-II (EDGF-II), α-heparin-binding growth factor (α-HGF), acidic hypothalmus-derived growth factor (acidic HDGF), and retina derived growth factor (RDGF).

38. A method according to claim 27 in which the normal human diploid lung fibroblast cell culture is selected from WI-38, MRC-5, IMR-90 an IMR-91.

39. A method according to claim 27 in which the normal human diploid lung fibroblast cell culture is WI-38.

* * * * *